United States Patent [19]
Pflugfelder et al.

[11] Patent Number: 6,153,607
[45] Date of Patent: Nov. 28, 2000

[54] NON-PRESERVED TOPICAL CORTICOSTEROID FOR TREATMENT OF DRY EYE, FILAMENTARY KERATITIS, AND DELAYED TEAR CLEARANCE (OR TURNOVER)

[75] Inventors: Stephen C. Pflugfelder; Scheffer C. G. Tseng; Andrew J. W. Huang, all of Miami, Fla.

[73] Assignee: University of Miami, Miami, Fla.

[21] Appl. No.: 08/754,060

[22] Filed: Dec. 4, 1996

Related U.S. Application Data

[60] Provisional application No. 60/007,917, Dec. 4, 1995.

[51] Int. Cl.$^7$ ..................................................... A67K 31/56
[52] U.S. Cl. ........................... 514/178; 514/177; 514/912
[58] Field of Search ................................... 514/177, 178, 514/912

[56] References Cited

U.S. PATENT DOCUMENTS

| | | |
|---|---|---|
| Re. 34,578 | 4/1994 | Lubkin . |
| 4,304,765 | 12/1981 | Shell et al. . |
| 4,407,792 | 10/1983 | Schoenwald et al. . |
| 4,448,774 | 5/1984 | Clemente et al. . |
| 4,474,751 | 10/1984 | Haslam et al. . |
| 5,041,434 | 8/1991 | Lubkin ..................................... 514/182 |
| 5,252,318 | 10/1993 | Joshi et al. . |
| 5,340,572 | 8/1994 | Patel et al. . |
| 5,620,921 | 4/1997 | Sullivan ................................... 514/178 |

FOREIGN PATENT DOCUMENTS

WO 94/17785  8/1994  WIPO .

OTHER PUBLICATIONS

Holly FJ et al, Tear Physiology and dry eyes. Review. Survey Opthalmol. 1977; 22:69–87.

Holly FJ., Formation and stability of the tear film. Int. Ophthalmol. Clin. 1973; 13:73–96.

Murillo–Lopez et al, Dry Eyes in Cornea, Krachmer, Mannis, Holland (editors) St. Louis, Mosby, 1996 (Galley); Chapter 56 pp 663–686.

Pflugfelder et al. The autoimmune nature of aqueous tear deficiency; Ophthalmology 1986;93:1513–1517.

Pflugfelder et al, Conjunctival cytological features of primary Sjogren's Syndrome; Ophthalmology 1990;97:985–991.

Pflugfelder et al, B. Coorelation of conjunctival globlet cell...ocular irritation; Ophthalmology; Feb. 1997:223–235.

Hideji et al, Confocal microscopic studies . . . benzalkonium chloride. Cornea. 1992; 11:221–225.

Ubels et al, Effects of preservative–free ... epithelial structure and function. Arch Ophthalmol. 1995; 113:371–378.

Lee et sl, Glucocorticosteriods selectively inhibit ... mRNA, Proc Natl Acad Sci USA 1988; 85:1204–8.

Zanler et al, Evidence tha glucocorticosteriods block . . . accessory cells; Transplantation 1990; 49:183–185.

Marron et al, Alterations in renal interleukin–1 . . . rejection in the rat; Transplantation 1993; 56:1157–1162.

Hall et al, Effects of Intravenous methylprednisolone . . . in the cat; J. Neurosurg 1982; 57:247–253.

Anderson et al, Lipid hydrolysis...selenium. CNS Trauma 1985; 2:257–267.

"Ocular Anti–Inflammatory Agents"; Pharmaceuticals; PDR for Ophthalmology.

Jones et al; Sjogren's Syndrome: "Cytokine and Opstein . . . Epithelium"; Investigative Ophthalmology & Visual Science, Aug. 1994, vol. 35, No. 9 p. 3493–3504.

Wright, "Filamentary Keratitis", Trans. Ophthal. Soc. UK (1975) 95, pp. 260–266.

*Primary Examiner*—Zohreh Fay
*Attorney, Agent, or Firm*—Cushman Darby & Cushman IP Group of Pillsbury Madison & Sutro

[57] ABSTRACT

A preservative-free composition containing an effective amount of a corticosteroid in an aqueous carrier to treat a dry eye condition. The composition may be provided as a part of a therapeutic regimen to treat a variety of dry eye conditions and ocular surface disorders manifesting delayed tear clearance previously not readily treatable. The composition may be packaged as containers of single dosage amounts of the corticosteroid-aqueous composition sufficient for pulsed-therapy of acute exacerbations of the irritation symptoms and ocular surface disease of conditions associated with dry eye and delayed tear clearance.

7 Claims, No Drawings

NON-PRESERVED TOPICAL CORTICOSTEROID FOR TREATMENT OF DRY EYE, FILAMENTARY KERATITIS, AND DELAYED TEAR CLEARANCE (OR TURNOVER)

Thus application claims the benefit of U.S. Provisional Application No. 60/007,917, filed Dec. 4, 1995.

BACKGROUND OF THE INVENTION

1. Field of Invention

The invention relates to the field of pharmacology, in particular the treatment of dry eye syndrome and ocular surface disorders with delayed tear clearance using corticosteroid.

2. Description of Related Art

The human ocular surface is normally covered by a tear film that is composed of a superficial thin lipid layer (primarily derived from meibomian gland secretions), a middle bulk aqueous layer (consisting of proteins, electrolytes, and water secreted by lacrimal glands), and the innermost mucus layer derived from mucins secreted by the ocular surface epithelial cells.[1]

A stable tear film ensures comfort and serves as the refractive optical surface of the eye. Furthermore, the tear film serves as a barrier for the ocular surface against microbial infection and inflammation from mechanical trauma.[1,2] Tear film deficiencies, referred to as dry eye, are a common clinical problem that can result from decreased secretion of tears by the lacrimal gland and/or increased evaporative loss due to a deficient lipid layer or blink abnormalities.[3] Patients with mild dry eye complain of annoying eye irritations. Those with severe dry eye, such as Sjögren's syndrome, may experience constant and disabling eye irritation, and develop ocular surface epithelial disease and sight-threatening sterile or microbial corneal ulceration.[4] The other reason that ocular irritation can occur is when the clearance of tears is delayed. Delayed tear clearance can be found in a number of other ocular surface disorders. Delayed tear clearance results in the accumulation of ocular irritants which can be derived from the environment (pollutants), medications (or preservatives), and cells (inflammatory mediators—to be described later).

For years it has been recognized that patients with dry eye develop pathologic changes of the ocular surface epithelial cells termed squamous metaplasia. Unreported research suggests that this process is the result of increased proliferation, abnormal differentiation, and inflammation of the ocular surface epithelial cells. In contrast to normal cells, these metaplastic cells do not produce the mucus that normally coats the ocular surface and forms a barrier against infection and mechanical trauma. This renders the ocular surface susceptible to damage from the mild trauma of desiccation blinking, rubbing, and foreign bodies (such as contact lenses).

In 1990, it was reported that a significantly greater percentage of patients with aqueous tear deficient dry eye than normal controls showed inflammatory cell infiltration of their conjunctival epithelium, and based on this finding, it was speculated that inflammation plays an important role in the pathogenesis of the conjunctival epithelial squamous metaplasia that develops in dry eye.[5] This hypothesis was confirmed by the abnormal production of an immune activation marker, intercellular adhesion molecule 1 (ICAM-1), and the inflammatory cytokine interleukin 6 (IL-6) by the conjunctival epithelial cells of patients with aqueous tear deficiency.[6] Expression of HLA-DR antigen by the conjunctival epithelium in the majority of patients (60%) with ocular irritation associated with aqueous tear deficiency as well as meibomian gland disease was subsequently noted, and these findings suggest that inflammation of the conjunctival epithelium may be the underlying cause for the ocular irritation experienced by patients suffering from all types of dry eye.[7] It is likely that this inflammation is enhanced when tear clearance is delayed.

Artificial tears are the current mainstay of therapy for dry eye.[3] They are aqueous solutions containing a number of different synthetic polymers to enhance their retention time on the ocular surface, and are available in both preserved and non-preserved formulations (summarized in Table 1). Although artificial tears provide temporary symptomatic improvement (typically 10 minutes or less), they have not been found to be effective in treating conjunctival squamous metaplasia.

Dry eye has not traditionally been considered to be an inflammatory disease. It is likely that practitioners have not considered the use of anti-inflammatory therapy for this reason as well as the potential risk of infection, corneal ulceration, elevated intraocular pressure, and cataract formation that may be associated with the use of topically applied corticosteroid. Our current concepts regarding the pathogenesis of the ocular surface disease and irritation that accompany syndromes with dry eye and delayed tear clearance suggested to us that the use of non-preserved topical corticosteroid may be effective, particularly for "pulse therapy" of the acute exacerbations that these patients often have.

The contents of all the documents cited herein are expressly incorporated by reference.

SUMMARY OF THE INVENTION

An object of this invention is to provide a preservative-free composition containing an effective amount of a corticosteroid in a carrier to treat a dry eye condition. A further object of this invention is a therapeutic regimen to treat a variety of dry eye conditions and ocular surface disorders manifesting delayed tear clearance previously not readily treatable. A still further object of the invention is to provide a packaged container of single dosage forms of the corticosteroid-vehicle composition sufficient for pulsed-therapy of acute exacerbations of the irritation symptoms and ocular surface disease of conditions associated with dry eye and delayed tear clearance.

The presence of conjunctival epithelial inflammation in dry eye patients coupled with the fact that topically applied corticosteroid are the mainstay of treatment for psoriasis, an inflammatory condition of the skin with pathologic features similar to those found in the conjunctiva of Sjögren's syndrome patients, lead to the evaluation of topical corticosteroid for the treatment of dry eye and resulted in the disclosed invention.

Corticosteroid suitable for use in the invention include methylprednisolone sodium succinate (0.1–1%), prednisolone acetate (0.1–1%), prednisolone sodium phosphate (0.1–1%), fluorometholone (0.1–0.5%), fluorometholone acetate (0.1–0.5%), dexamethasone sodium phosphate (0.1–0.5%) hydroxymethyl-progesterone (0.1–1%), rimexolane (0.1–1%), budesonide (0.1–1%), and tixocortol pivalatein (0.1–1%) in concentrations of approximately 0.1 to approximately 1%.

A drop (20–50 µl) will be applied to the surface of the eye from a sterile unit dose container. This solution will then mix with the tear fluid and bath the diseased ocular surface cells.

The preparations can be administered in any conventional manner, e.g. topically to the eye. See generally Maurice DA and Mishima S. Ocular Pharmacolinetics in *Pharmacology of the Eye* (M. L. Sears, editor)–Springer-Verlag, Berlin; 1984, pp. 19–24.

Other objects, features, and characteristics of the present invention as well as the methods of operation and functions of the related elements of structure, and the combination of parts and economies of manufacture, will become more apparent upon consideration of the following description and the appended claims with reference to the accompanying tables, all of which form a part of this specification.

DETAILED DESCRIPTION OF THE INVENTION

The preferred corticosteroid preparation for treating dry eye patients was a non-preserved aqueous solution of the synthetic corticosteroid, methylprednisolone sodium succinate [chemical name pregna-1,4-diene-3,20-dione,21-(3-carboxy-1-oxopropoxy)-11,17-dihydroxy-6-methyl-monosodium salt (6 alpha, 11β) methylprednisolone]. This agent was chosen for several reasons. First and foremost, methylprednisolone is a water soluble steroid that could be prepared as a non-preserved isotonic aqueous solution. There is an increasing trend in recent years toward the use of non-preserved artificial tears for the treatment of dry eyes. This is due to the finding that benzalkonium chloride, the preservative found in the majority of preserved artificial tears (Table 1) and commercially-available ocular corticosteroid (Table 2) produces several toxic effects on ocular surface epithelium including break-down of intercellular junctions, epithelial sloughing, and increase epithelial permeability.[8,9] The diseased conjunctival epithelium in dry eye patients already shows increased permeability and with the altered capacity to clear topically applied preservatives from the ocular surface (due to reduced tear flow and/or reduced drainage), dry eye patients are extremely susceptible to toxicity from preservative-containing eyedrops. Administration of preserved artificial tears several times per day to dry eye patients frequently leads to increased irritation symptoms and worsening of their ocular surface disease. Intravenous administration of aqueous solutions of methylprednisolone has well documented efficacy and minimal toxicity for the treatment of systemic inflammatory disease. Therefore, this agent seemed ideally suited for topical application to the eye in a non-preserved aqueous solution.

The second reason methylprednisolone was chosen for treatment of dry eye is because of its documented anti-inflammatory properties. Methylprednisolone has been reported to decrease expression of proinflammatory and inflammatory cytokine mRNA including IL-1 and IL-6.[10,11] This steroid has also been reported to decrease secretion of preformed cytokines by cells.[12] Furthermore, high doses of methylprednisolone have the unique capability of inhibiting lipid peroxidation in, and blocking release of free fatty acids and eicosanoids (inflammatory molecules) from injured neural tissue.[13,14] For these reasons, methylprednisolone is currently the steroid of choice for therapy of transplant rejection, severe systemic autoimmune disease, optic neuritis, and spinal cord trauma.

The currently approved corticosteroid for treatment of eye disease are summarized in Table 2. All of these preparations contain the preservative benzalkonium chloride, and none use methylprednisolone as their active ingredient. Dry eye patients are treated with a topical non-preserved aqueous solution of methylprednisolone. This was formulated by diluting intravenous methylprednisolone sodium succinate in nonpreserved sterile normal saline solution. Patients with filamentary keratitis (a painful ocular surface condition often associated with dry eye) not responding to conventional therapy with topical non-preserved artificial tear have also been treated according to the invention. Encouraging success has also been observed in treating patients suffering from delayed tear clearance according to the invention.

To date, 12 cases of aqueous tear deficiency associated with Sjögren's syndrome have been treated with topical non-preserved methylprednisolone. The details of these patients is summarized in Table 3. All of these patients were experiencing exacerbations of their condition with moderate to severe irritation symptoms despite the use of conventional non-preserved artificial tear therapy prior to the treatment with topical 1% methylprednisolone three-to-four times per day for two weeks. Two subjects (numbers 1 and 9, Table 3) had previously been treated with preserved topical steroids with minimal or no symptomatic improvement. In all cases, symptoms of irritation, light sensitivity, and mucous discharge were markedly reduced or eliminated after 2 weeks of this methylprednisolone therapy. Patients reported that their urge to instill artificial tear drops to relieve their irritation symptoms decreased dramatically (in many cases from 10 to 15 times per day to once or twice per day). Objective improvement of ocular surface disease was also noted following several weeks of methylprednisolone therapy, as evidenced by reduced ocular surface rose bengal and fluorescein staining scores, and reduction or elimination of corneal epithelial filaments and mucus strands. Symptomatic relief was maintained in most patients after reduction of the methylprednisolone concentration to 0.5 %, administered twice daily. Therapy was discontinued in some patients after 1–2 months, while others have continued on low dose therapy under strict medical supervision.

Ocular irritation symptoms also improved in the majority of patients with ocular irritation associated with delayed tear clearance who were treated with topical non-preserved methylprednisolone. A total of 69 cases (121 eyes) have been treated with methylprednisolone 3 times per day for 3 weeks (Table 4). Before treatment, these patients complained of tearing (59%), itching (26%), burning (26%), redness (21%), foreign body sensation (20%), and mucous discharge (20%); some patients experienced more than one complaint. They had been treated with a variety of different topical medications including artificial tears (51%), conventional preserved steroids (51%), antibiotics (25%) and vasoconstrictors (18%); some patients used more than one type of medication. Out of those who received non-steroid treatments, only 22.6% showed some improvement by past history. After the non-preserved methylprednisolone treatment, 84.1% of patients or 97.5% of eyes revealed subjective improvement with notable reduction or elimination of ocular irritation. Furthermore, 81.2% of patients or 90.9% of eyes showed objective improvement with reduction or elimination of conjunctival redness. More importantly, in all cases the fluorescein clearance test showed delayed tear clearance before treatment, but after treatment, 88.4% of cases showed improvement of tear clearance. These results support the notion that delayed tear clearance is pathogenetic, and that topical non-preserved methylprednisolone is effective to treat ocular diseases or irritation associated with delayed tear clearance. Similar to the patients with aqueous tear deficiency, symptomatic relief was maintained for this group of patients after the methylprednisolone concentration was reduced to 0.5%.

Three patients with post-surgical filamentary keratitis that did not respond to conventional therapy experienced total resolution of these lesions within two weeks of initiation of topical 1% methylprednisolone therapy (Table 5).

Although not evaluated, nonpreserved aqueous solutions, suspensions, or gels of other corticosteroid including prednisolone acetate, prednisolone sodium phosphate, fluorometholone, fluorometholone acetate, dexamethasone sodium phosphate, hydroxymethyl-progesterone, rimexolane, budesonide, and tixocortol pivalate are expected to exhibit efficacy similar to that of methylprednisolone for the treatment of dry eye, filamentary keratitis, and ocular diseases with delayed tear clearance. Corticosteroids such as fluorometholone with lower propensity to elevate intraocular pressure due to more rapid metabolism and/or shorter half-life may have advantages for long-term low dose therapy of dry eye and ocular surface diseases associated with delayed tear clearance.

While the invention has been described in connection with what is presently considered to be the most practical and preferred embodiment, it is to be understood that the invention is not to be limited to the disclosed embodiment, but on the contrary is intended to cover various modifications and equivalent arrangements included within the spirit and scope of the appended claims.

The content of all of the following references are expressly incorporated herein by reference.

REFERENCES

1. Holly FJ, Lemp MA. Tear physiology and dry eyes. Review. Survey Ophthalmol 1977; 22:69–87.
2. Holly FJ. Formation and stability of the tear film. Int. Ophthalmol Clin. 1973:13:73–96.
3. Murillo-Lopez F and Pflugfelder SC. Dry Eyes in CORNEA, Krachmer J, Mannis M, Holland E (editors) St Louis, Mosby 1996; Chapter 56 pp 663–686.
4. Pflugfelder SC, Wilhelmus KR, Osato MS, Matoba AY, Font RL: The autoimmune nature of aqueous tear deficiency. Ophthalmology 1986; 93:1513–1517.
5. Pflugfelder SC, Huang AJW, Schuclovski PT, Pereira IC, Tseng SCG. Conjunctival cytological features of primary Sjogren's Syndrome. Ophthalmology 1990; 97: 985–991.
6. Jones DT, Yen M, Monroy D, Ji X, Atherton SS, Pflugfelder SC. Evaluation of cytokine expression in the conjunctival epithelia of Sjogren's syndrome patients. Invest Ophthalmol Vis Sci 1994; 35:3493–3504.
7. Pflugfelder SC, Tseng SCG, Yoshino K, Monroy D, Felix C, Reis B. Correlation of conjunctival goblet cell density (GCD) and mucosal epithelial mucin (MEM) expression in patients with ocular irritation. Ophthalmology 1996 (in press)
8. Hideji I, Petroll WM, Jester JV, Cavanaugh DH. Confocal microscopic studies of living rabbit cornea treated with benzalkonium chloride. Cornea 1992; 11:221–225.
9. Ubels JL, McCartney MD, Lantz WK, Beaird J, Dayaln A, Edelhauser HF. Effects of preservative-free artificial tear solutions on corneal epithelial structure and function. Arch Ophthalmol 1995; 113:371–378.
10. Lee SW, Tsou AP, Chan H, et al. Glucocorticosteroids selectively inhibit the transcription of interleukin-1 β gene and decrease the stability of interleukin-1 β mRNA. Proc Natl Acad Sci USA 1988; 85:1204–8.
11. Zanier B, Walz G, Wieder KJ, Strom TB. Evidence that glucocorticosteroids block expression of the human interleukin-6 by accessory cells. Transplantation 1990; 49:183–185.
12. Marron RB, Sundar SK, Sanfilippo FB, Coffman TM. Alterations in renal interleukin-1 production during kidney transplant rejection in the rat. Transplantation 1993; 56:1157–1162.
13. Hall ED, Braughler JM. effects of intravenous methylprednisolone on spinal cord lipid peroxidation and (Na+ K)-ATPase activity. Dose-response analysis during 1st hour after contusion injury in the cat. J Neurosurg 1982; 57:247–253.
14. Anderson DK, Saunders RD, Demediuk P et al. Lipid hydrolysis and peroxidation in injured spinal cord: partial protection with methylprednisolone or vitamin E and selenium. CNS Trauma 1985; 2:257–267.

TABLE 1

APPROVED MEDICATIONS FOR DRY EYE (ARTIFICIAL TEAR DROPS)

| Trade Name (Manufacturer) | Major Components | Preservative |
| --- | --- | --- |
| A. PRESERVED DROPS | | |
| Adsorbotears (Alcon) | HEC, povidone | thimerosal, EDTA |
| Akwa Tears (Akorn) | PVA, NaCt | BAK, EDTA |
| Artificial Tears (Rugby) | PVA | BAK. EDTA |
| Comfort Tears (Barnes-Hinds) | HEC | BAK, EDTA |

TABLE 1-continued

APPROVED MEDICATIONS FOR DRY EYE (ARTIFICIAL TEAR DROPS)

| Trade Name (Manufacturer) | Major Components | Preservative |
|---|---|---|
| A. PRESERVED DROPS | | |
| Dakrina (Dakryon) | PVA, povidone, vitamin A palmitate, vitamin C | potassium sorbate, EDTA |
| Dwette (Dakryon) | PVA, poly-N-glucose | potassium sorbate, EDTA |
| Eye-Lube-A (Optopics) | Glycerine | BAK, EDTA |
| Hypotears (CIBA Vision) | PVA. PEG 400, dextrose | BAK, EDTA |
| tsopto Alkaline (Alcon) | HPMC | BAK |
| tsopto Tears (Alcon) | HPMC | BAK |
| Lacrit (Allergan) | HPMC gelatin A, polysorbate 80 dextrose | Chlorobutanol |
| Liquifilm Forte (Allergan) | PVA | Thimerosal, EDTA |
| Liquifilm Tears (Allergan) | PVA | Chlorobutanol |
| Lubri Tears (B&L) | HPMC, dextran 70 | BAK, EDTA |
| Moisture Drops (B&L) | HPMC, dextran, glycerin | BAK |
| Murine (Ross) | PVA, povidone | BAK, EDTA |
| Murocet (B&L) | MC, propylene glycol | Methylparaben, Polyparaben |
| Nu-Tears (Optopics) | PVA, PEG-400 | BAK, EDTA |
| Nutra Tears (Dakryon) | PVA, vitamin B12 | BAK, EDTA |
| Tear Guard (Medtech) | HEC | Sorbic acid, EDTA |
| Tearisot (CIBA Vision) | HPMC | BAK, EDTA |
| Tears Naturate (Alcon) | HPMC, dextran 70 | BAK, EDTA |
| Tears Naturate II (Alcon) | HPMC, dextran 70 | Polyquaternium, EDTA |
| Tears Plus (Allergan) | PVA, povidone | Chlorobutanol |
| Tears Renewed (Akorn) | HPMC, dextran 70 | BAK, EDTA |
| Ultra Tears (Alcon) | HPMC | BAK |
| B. NON-PRESERVED DROPS | | |
| Bion (Alcon) | HPMC, dextran 70 | none |
| Celluvisc (Allergan) | CMC | none |
| Hypotears PF (CIBA Vision) | PVA, PEG 400, dextrose | none |
| Refresh (Allergan) | PVA, povidone | none |
| Refresh Plus (Allergan) | CMC | none |
| Tears Naturate Free (Alcon) | HPMC, dextran 70 | none |

HEC: hydroxyethylcellulose, HPMC: hydroxypropylmethylcellulose, MC: methylcellulose, PVA; polyvinyl alcohol, CMC: carboxymethylcellulose, EDTA: ethylenediaminetetraacetic acid; BAK: benzalkonium chloride

TABLE 2

TOPICAL OPHTHALMIC GLUCOCORTICOSTEROID DROPS

| Chemical Name | Trade Name (Manufacturer) | Concentration | Preservative |
|---|---|---|---|
| Dexamethasone suspension | Maxidex (Alcon) | 0.1% | BAK |
| Dexamethasone sodium phosphate solution | AK-DEX (Alcon) | 0.1% | BAK |
|  | Decadron (Merck) | 0.1% | BAK |
| Fluoromethalone suspension | Fluor-op (Ahorn) | 0.1% | BAK |
|  | FML (Allergan) | 0.1% | BAK |
|  | FML-forte (Allergan) | 0.25% | BAK |
| Fluoromethalone Acetate suspension | Flarex (Alcon) | 0.1% | BAK |
|  | Eflone (CIBA Vision) | 0.1% | BAK |
| Medrysone suspension hydroxymethyl progesterone) | HMS (Allergan) | 1% | BAK |
| Prednisone Acetate Suspension | Pred Mild (Allergan) | 0.12% | BAK |
|  | Econopred (Alcon) | 0.125% | BAK |
|  | Econopred plus (Alcon) | 1% | BAK |
|  | Pred forte (Allergan) | 0.125% | BAK |
| Prednisone Sodium Phosphate Solution | AK-pred (Ahorn) | 0.125% | BAK |
|  | Inflamase (CIBA Vision) | 0.125% | BAK |
|  | AK-pred (Ahorn) | 1% | BAK |
|  | lnflamase forte (CIBA Vision) | 1% | BAK |
| Rimexotane | Vexol (Alcon) | 1% | BAK |

BAK: benzalkonium chloride

TABLE 3

NON-PRESERVED METHYLPREDNISOLONE
THERAPY FOR AQUEOUS TEAR DEFICIENCY

| Patient Number | Initials | BPEI # | Age/Gender | Therapy Initiated | Cause of ATD | Prior Therapy | Therapeutic Response | | |
|---|---|---|---|---|---|---|---|---|---|
| | | | | | | | Symptoms[1] | Oscular Surface Disease[2] | |
| | | | | | | | | Right Eye | Left Eye |
| 1 | LO | 460919 | 44/F | 08/21/95 | Primary SS | Hypotears PF Alomide, Flarex | 3+ | Not eval | Not eval |
| 2 | NQ | 428890 | 48/F | 03/22/95 | Primary SS | Hypotears PF | 3+ | 3+ | 3+ |
| 3 | JM | 493712 | 50/F | 03/17/95 | Secondary SS (RA) | Bion | 2+ | 1+ | 3+ |
| 4 | BB | 508517 | 77/F | 06/06/95 | Primary SS | Celluvisc, Duolube Hypotears + Healon | 3+ | Not eval | Not eval |
| 5 | JW | 484077 | 45/M | 04/03/95 | Primary SS | Celluvisc, oral CSA Bromhexine | 2+ | 2+ | 2+ |
| 6 | MF | 515472 | 67/F | 07/26/95 | Secondary SS (RA) | Hypotears, PF, mucomyst, Refresh plus | 2+ | 2+ | 3+ |
| 7 | TV | 498460 | 53/M | 01/30/95 | Primary SS | Refresh plus Duolube ointment | 2+ | 3+ | 1+ |
| 8 | EB | 285663 | 69/F | 02/13/95 | Primary SS | Hypotears PF | 2+ | 3+ | 2+ |
| 9 | JF | 493759 | 36/F | 12/23/94 | Primary SS | Pred Forte, Aquasite | 3+ | 3+ | 3+ |
| 10 | JB | 226567 | 65/F | 01/19/95 | Primary SS | Bion | 3+ | 3+ | 3+ |
| 11 | BC | 373034 | 53/F | 12/16/94 | Primary SS | Vitamin A Refresh plus | 2+ | 3+ | 3+ |
| 12 | MV | 368754 | 62/F | 03/13/95 | Primary SS | Refresh plus | 3+ | 3+ | 2+ |

Legend: SS = Sjogren Syndrome, CSA
[1]1+ = slight improvement, 2+ = moderate improvement, 3+ = complete relief
[2]After 2 weeks of therapy, decrease in rose bengal staining score by 1 point = 1+, 2 points = 2+, 3 points or resolution of filamentary keratitis = 3+

TABLE 4

RESULTS OF NON-PRESERVED METHYLPREDNISOLONE
TREATMENT OF OCCULAR SURFACE DISEASES WITH
DELAYED TEAR CLEARANCE (126 EYES IN 70 PATIENTS)

| | Improved (%) | No Improvement (%) |
|---|---|---|
| Subjective[1] | 103 (82) | 23 (18) |
| Objective[2] | 100 (79) | 26 (21) |

[1]= decreased symptoms of ocular irritation
[2]= decreased lid and ocular surface redness

TABLE 5

NON-PRESERVED METHYLPREDNISOLONE
FOR TREATMENT OF FILAMENTARY KERATITIS

| Number | Patient | BPEI # | Age/Gender | Date of Treatment | Cause[1] | Prior Therapy[2] | Response | |
|---|---|---|---|---|---|---|---|---|
| | | | | | | | Symptoms[3] | Filaments[4] |
| 1 | FB | 513704 | 90/F | 06/28/95 | 3 mos post phacol/IOL | Tobradex Hypotears | 3+ | 3+ |
| 2 | BM | 499158 | 71/F | 02/27/95 | 15 mos post phacol/IOL | Celluvisc | 3+ | 3+ |
| 3 | JC | 77323 | 82/M | 08/21/95 | 5 years post PK | Pred Forte topical CSA | NC | 3+ |

[1]phaco = phacoemulsification, PK = penetrating keratoplasty
[2]CSA = cyclosporin
[3]1+ = slight improvement, 2+ = moderate relief, 3+ = complete resolution of symptoms, NC = no change
[4]1+ = 10–50% decrease in number, 2+ = 51–99% decrease in number, 3+ = complete resolution

We claim:

1. A process for treatment of an ocular disease associated with delayed tear clearance or a dry eye condition in a patient comprising the steps of (a) identifying a patient having an ocular disease associated with delayed tear clearance (turnover) or a dry eye condition suitable for treatment with a corticosteroid, and (b) topically administering to an eye of said patient a nonpreserved solution, suspension, or gel comprising an aqueous carrier and an amount of a corticosteroid sufficient to alleviate said delayed tear clearance or dry eye condition.

2. The process for treatment of an ocular disease associated with delayed tear clearance or a dry eye condition in a patient according to claim 1 wherein the corticosteroid is methylprednisolone sodium succinate.

3. The process for treatment of an ocular disease associated with delayed tear clearance or a dry eye condition in a patient according to claim 1 wherein the administering is done two to four times daily for a period of one day to four weeks.

4. The process for treatment of an ocular disease associated with delayed tear clearance or a dry eye condition in a patient according to claim 1 wherein the corticosteroid preparation is in a single dosage form.

5. The process for treatment of an ocular disease associated with delayed tear clearance or a dry eye condition in a patient according to claim 1 wherein the corticosteroid preparation is administered topically to the eye.

6. A process according to claim 1 wherein said ocular disease or dry eye condition is selected from the group consisting of Sjögren's and non-Sjögren's syndrome-associated aqueous tear deficient dry eye, dry eye associated with meibomian gland disease, filamentary keratitis associated with dry eye and superior limbic keratoconjunctivitis.

7. A process according to claim 1 wherein said corticosteroid is selected from the group selected from methylprednisolone sodium succinate, prednisolone acetate, prednisolone sodium phosphate, fluorometholone, fluorometholone acetate, dexamethasone sodium phosphate, rimexolane, budesonide, and tixocortol pivalatein in concentrations of 0.1 to 1%.

* * * * *